(12) United States Patent
Stadler

(10) Patent No.: US 6,475,505 B1
(45) Date of Patent: Nov. 5, 2002

(54) BIOCIDE-POLYESTER CONCENTRATES AND BIOCIDAL COMPOSITIONS PREPARED THEREFROM

(75) Inventor: Urs Stadler, Madison, NJ (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/467,809

(22) Filed: Dec. 20, 1999

(51) Int. Cl.$^7$ ............................................. A01N 25/10
(52) U.S. Cl. .................... 424/411; 424/409; 424/618; 424/630; 424/637; 424/638; 424/641; 424/78.09; 424/78.31; 424/78.37; 514/185; 514/187; 514/241; 514/721; 523/122
(58) Field of Search ................................ 424/405, 409, 424/404, 410, 411, 78.09, 78.31, 78.37, 618, 630, 637, 638, 641; 523/123; 514/721, 241, 185, 187

(56) References Cited

U.S. PATENT DOCUMENTS

| | | | |
|---|---|---|---|
| 4,663,359 A | | 5/1987 | Rei ............................. 521/85 |
| 4,686,239 A | | 8/1987 | Rei ............................. 521/55 |
| 4,744,976 A | * | 5/1988 | Snipes et al. ................ 424/408 |
| 5,229,124 A | * | 7/1993 | Rei ............................. 424/409 |
| 5,312,688 A | * | 5/1994 | Hongum et al. ............. 428/395 |
| 5,639,803 A | | 6/1997 | Anderson et al. ........... 523/122 |
| 5,702,754 A | * | 12/1997 | Zhong ........................ 427/2.12 |
| 5,919,554 A | | 7/1999 | Watterson, III et al. ..... 428/201 |
| 5,929,132 A | | 7/1999 | Hani et al. .................. 523/122 |

FOREIGN PATENT DOCUMENTS

| | | | |
|---|---|---|---|
| EP | 0843963 | | 5/1998 |
| GB | 2262468 | | 6/1993 |
| JP | 62544 | * | 1/1987 |
| WO | 92/07031 | | 4/1992 |
| WO | 92/0530 | * | 6/1992 |
| WO | 99/27792 | * | 6/1999 |
| WO | 00/53413 | | 9/2000 |

OTHER PUBLICATIONS

Hamex Annu. Tech. Conf—Soc. Plast. Eng 49th 1897–1900, 1991.*
Patent Abstracts of Japan 08239507 (1996).
Plastics Additives Handbook, 4$^{th}$ Ed., Gaechter, H. Mueller, Eds., Hanser Publishers, pp. 10–11 (1993).
"Encyclopedia of Chemistry Technology", vol. 21, John Wiley & Sons, New York, pp. 801–813.
Abstract for JP62000544 (1987).

* cited by examiner

Primary Examiner—Neil S. Levy
(74) Attorney, Agent, or Firm—Tyler A. Stevenson; Luther A. R. Hall

(57) ABSTRACT

Concentrates of various classical biocides in a polyester carrier resin when incorporated into a substrate resin, preferably a polyolefin such as polypropylene or polyethylene, provide the substrate polymer which biocidal activity with superior resistance to discoloration (yellowing) than when the biocide is directly incorporated into the substrate polymer as a powder at the same total concentration.

13 Claims, No Drawings

BIOCIDE-POLYESTER CONCENTRATES AND BIOCIDAL COMPOSITIONS PREPARED THEREFROM

The instant invention pertains to concentrates which comprise a biocidal compound and a polyester carrier resin. The addition of such concentrates into polymer substrates provides biocidal activity to said polymer substrate while preventing discoloration of the substrate.

BACKGROUND OF THE INVENTION

WO 92/07031 teaches the process for preparing a soluble-stable dispersion of a solid biocide comprising a swellable vinyl polymer with a liquid carrier to enable the incorporation of difficultly soluble biocides into polymer resins.

British Patent No. 2,262,468 describes the application of a composition comprising a biocide in a poly(vinyl alcohol) carrier medium to the surface of a mold or former in order to render a plastic article biocidally active during the manufacturing process.

Japanese Sho 62-000544 teaches the incorporation of an antibiotic by premixing it with poly(ethylene glycol) or silicone oil and melt blending the pre-mixture into a polyester resin or by preparing a master batch containing the antibiotic in a higher concentration and melting blending the master batch into the polyester.

While the process for putting biocides into plastics by adding the neat active biocidal compound into the polymer substrate during processing or manufacturing is known, this process can lead to discoloration of the final biocidally active substrate. The instant process involves preparing first a biocide-polyester concentrate which is then subsequently added to the polymer substrate. This leads to a final product which is both biocidally active and is resistant to discoloration.

OBJECTS OF THE INVENTION

One object of this invention provides for biocide-polyester concentrates useful for later incorporation into polymer substrates.

Another object of this invention provides for biocidally active polymer compositions resistant to discoloration made by the incorporation of said biocide-polyester concentrate into the polymer.

DETAILED DESCRIPTION

The instant invention pertains to a biocide-polyester concentrate which comprises
(A) 1–75% by weight of a biocide, and
(B) 99–25% by weight of a polyester carrier resin.

Preferably, component (A) is 10–50% by weight of a biocide, and component (B) is 90–50% by weight of a polyester carrier resin.

The biocide (A) is at least one compound selected from the group consisting of (a) halogenated organic compounds, such as 2,4,4'-trichloro-2'-hydroxydiphenyl ether (IRGASAN® or IRGAGUARD®, Ciba Specialty Chemicals Corp.);
(b) organosulfur compounds, such as methylenedithiocyanate, 2-N-octyl-4-isothiazolin-3-one, 3,5-dimethyl-tetrahydro-1,3,5-2H-thiodiazine-2-thione;
(c) s-triazine compounds, such as 2-methylthio-4-tert-butylamino-6-cyclopropyl-amino-s-triazine;
(d) copper or copper compounds, such as copper sulfate, copper nitrate, copper-bis(8-hydroxyquinoline);
(e) organotin compounds, such as tributyltin oxide and its derivatives; and
(f) bactericides, such as silver and zinc compounds, oxy-bis-phenoxyarsine.

The polyester carrier resin (B) is a homopolyester or a copolyester prepared from aliphatic, cycloaliphatic or aromatic dicarboxylic acids and diols or hydroxycarboxylic acids.

Preferably, the polyester of component (B) has dicarboxylic acid repeat units selected from the group consisting of aromatic dicarboxylic acids having 8 to 14 carbon atoms, aliphatic dicarboxylic acids having 2 to 40 carbon atoms, cycloaliphatic dicarboxylic acids having 6 to 10 carbon atoms, aliphatic hydroxycarboxylic acids having 2 to 12 carbon atoms, aromatic and cycloaliphatic hydroxycarboxylic acids having 7 to 14 carbon atoms, and mixtures thereof.

Preferably such aromatic diacids are terephthalic acid, isophthalic acid, o-phthalic acid, 1,3-, 1,4-, 2,6- and 2,7-naphthalenedicarboxylic acid, 4,4'-biphenyldicarboxylic acid, di(4-carboxyphenyl) sulfone, 4,4'-benzophenonedicarboxylic acid, 1,1,3-trimethyl-5-carboxy-3-(p-carboxyphenyl)indane, di(4-carboxyphenyl) ether, bis (p-carboxy-phenyl)methane and bis(p-carboxyphenyl) ethane.

Most preferably, the aromatic diacids are terephthalic acid, isophthalic acid and 2,6-naphthalenedicarboxylic acid.

Suitable aliphatic dicarboxylic acids are linear or branched. Preferably such aliphatic dicarboxylic acids are oxalic acid, malonic acid, succinic acid, glutaric acid, adipic acid, pimelic acid, trimethyladipic acid, sebacic acid, azelaic acid and dimeric acids (products of the dimerization of unsaturated, aliphatic acids such as oleic acid), alkylated malonic acid, alkylated succinic acid, and mixtures thereof.

Suitable cycloaliphatic dicarboxylic acids are 1,3-cyclobutanedicarboxylic acid, 1,3-cyclopentanedicarboxylic acid, 1,3- and 1,4-cyclohexanedicarboxylic acid, 1,3- and 1,4-(dicarboxymethyl)cyclohexane and 4,4'-dicyclohexyldicarboxylic acid.

The diol or glycol portion of the polyester of component (a) are derived from the generic formula HO-R-OH where R is an aliphatic, cycloaliphatic or aromatic moiety of 2 to 18 carbon atoms.

Preferably such diols or glycols are ethylene glycol, diethylene glycol, triethylene glycol, 1,2- and 1,3-propane-diol, 1,2-, 1,3-, 2,3- and 1,4-butane-diol, pentane-1,5-diol, neopentane glycol, hexane-1,6-diol, dodecane-1,12-diol, 1,4-cyclohexanedimethanol, 3-methylpentane-2,4-diol, 2-methylpentanel, 4-diol, 2,2-diethylpropane-1,3-diol, 1,4-di-(hydroxyethoxy)benzene, 2,2-bis(4-hydroxycyclohexyl)-propane, 2,4-dihydroxy-1,1,3,3-tetramethylcyclobutane, 2,2-bis-(3-hydroxyethoxyphenyl)propane, 2,2-bis-(4-hydroxypropoxyphenyl)ethane, 1,4dihydroxycyclohexane, p-xylylene glycol, poly(ethylene glycol), poly(propylene glycol), and mixtures thereof.

Preferably, the diol is 1,4-dihydroxycyclohexane, 1,4-cyclohexanedimethanol, ethylene glycol, 1,4-butanediol, 1,2-propylene glycol and 1,3-trimethylene glycol.

Most preferably, the diol is ethylene glycol.

It is furthermore possible for the polyester to be branched by small amounts, for example 0.1 to 3 mol %, based on the dicarboxylic acid present, of monomers having a functionality greater than two, e.g. pentaerythritol, trimellitic acid, 1,3,5-tri(hydroxyphenyl)benzene, 2,4dihydroxybenzoic acid or 2-(4-hydroxyphenyl-2-(2,4-dihydroxyphenyl)propane.

In the polyester comprising at least two monomers, the polymer can have randomly distributed units or units arranged in the form of blocks.

The polyester of component (B) is preferably poly (ethylene terephthalate) PET, poly(ethylene 2,6-naphthalene-2,6dicarboxyiate) PEN or poly(ethylene/1,4-cyclo-hexylenedimethylene terephthalate) PETG copolyester, EASTAR® 6763, Eastman Chemical); most preferably, poly(ethylene terephthalate) or the poly (ethylene/1,4-cyclo-hexylenedimethylene terephthalate) copolyester.

It is also contemplated that the polyester of component (B) can also be a blend of polyesters or copolyesters including components mentioned above.

The instant invention also pertains to biocidally active polymer compositions resistant to discoloration which comprise (I) a polymer substrate, and (II) an effective biocidal amount of a concentrate described above.

The effective biocidal amount of the active component is 0.01 to 5% by weight based on the total composition.

The instant invention also relates to a process for preparing a biocidally active polymer composition, which is resistant to discoloration, which comprises incorporating into said polymer an effective biocidal amount of a concentrate described above.

The polymer substrate of component (I) is a polyolefin, polystyrene, polyamide, polycarbonate, a polystyrenic such as ABS, SAN, ASA, a nylon (a polyamide), a polyurethane, an acrylate, a polyacrylonitrile a rubber modified styrenic, poly(vinyl chloride), poly(vinyl butyral) or a polyacetal (polyoxymethylene).

Preferably, the polymer substrate is a polyolefin or a polystyrenic, especially polypropylene or polyethylene, most especially linear low density polyethylene (LLDPE), low density polyethylene (LDPE) and high density polyethylene (HDPE).

The incorporation of the instant biocide-polyester concentrate into the polymer substrate affords a number of real advantages over using a neat biocide for the same purpose. These advantages are a. better handling;

b. improved industrial hygiene and environmental concerns; and c. improved control of dosing accuracy for insertion of biocide into the polymer substrate.

Most of all and surprising is the advantage that the use of the biocide-polyester concentrate, when added to a variety of polymer substrates, leads to resistance to discoloration in the biocidally active polymer substrate as compared to the incorporation of neat biocide directly into the polymer substrate.

The following examples are meant for illustrative purposes only and are not to be construed to limit the scope of the instant invention in any way whatsoever.

EXAMPLE 1

Preparation of Biocide-Polyester Concentrate

A commercial poly(ethylene/1,4-cyclohexylenedimethylene terephthalate) PETG copolyester (EASTAR® 6763, Eastman Chemical), is predried in vacuo under nitrogen in an oven at about 70° C. to a moisture level of about 30 ppm as verified on a Mitsubishi VA-06 moisturemeter. 75 Parts by weight of this dried resin is dry blended with 25 parts by weight of 2,4,4'-trichloro-2'-hydroxydiphenyl ether (IRGASAN® or IRGAGUARD®, Ciba Specialty Chemicals Corp.). The blended resin is then melt compounded under nitrogen into pellets at 1 80° C. using a Leistritz extruder with corotating, non-intermeshing twin screw at 100 rpm.

EXAMPLE 2

Prepartion of Biocidally Active Composition Using a Biocide-Polyester Concentrate Polypropylene homopolymer (PRO-FAX® 6501, Montell Polyolefins, 100parts), stabilized with 0.05 parts of neopentanetetrayl tetralis(3,5-di-tert-butyl-4-hydroxyhydrocinnamate), 0.10 parts of tris(2,4-di-tert-butylohenyl) phosphite and 0.05 parts of calcium stearate is dry blended without a biocide; or with 0.25 parts or with 0.50 parts of 2,4,4'-trichloro-2'-hydroxydiphenyl ether (IRGASAN® or IRGAGUARD®, Ciba Specialty Chemicals Corp.) either as a neat powder or as a concentrate as prepared in Example 1. The parts of components are by weight.

These various mixtures are melt compounded in one, two and three passes at two different temperatures [500° F. (260° C.) and 550° F. (288° C.)] in a Superior/MPM extruder using a 24:1 L/D screw with a Maddock mixing head at 80 rpm.

The extruded pellets are compression molded into 125 mil plaques (2"×2", 5.08 cm×5.08 cm) at 450° F. (232° C.) for nine minutes (three minutes at low pressure; three minutes at high pressure; three minutes cooling). Yellowness index (YI) values are determined on the plaques according to ASTM D1925 on a DCI SF600 spectrophotometer. An increase in yellowness corresponds to a positive increase in the YI value.

The results are given in the table below.

| (Biocide % Sample by wt) | Yellowness Index (YI) after multiple pass extrusion at 500° F. (260° C.) | | |
|---|---|---|---|
| | First | Second | Third |
| Control (none) | 7.8 | 9.4 | 14.5 |
| Powder (0.25%) | 8.4 | 8.8 | 9.7 |
| Powder (0.50%) | 8.8 | 9.7 | 9.2 |
| Concentrate (0.25%) | −0.4 | −2.0 | −0.6 |
| Concentrate (0.50%) | −0.1 | −0.2 | 0.0 |

| (Biocide % Sample by wt) | Yellowness Index (YI) after multiple pass extrusion at 550° F. (288° C.) | | |
|---|---|---|---|
| | First | Second | Third |
| Control (none) | 10.4 | 11.9 | 10.4 |
| Powder (0.25%) | 6.4 | 6.3 | 6.6 |
| Powder (0.50%) | 7.1 | 7.2 | 7.4 |
| Concentrate (0.25%) | 0.3 | −2.3 | −0.7 |
| Concentrate (0.50%) | −1.8 | −1.1 | 0.5 |

These results clearly show that the plaques which contain the biocide incorporated therein using the concentrate are far superior in color performance (much lower YI values) than the plaques containing the same concentration of biocide added as a neat powder.

EXAMPLE 3

Prepartion of Biocidally Active Composition Comparing a Biocide-Polyester Concentrate with a Biocide-Polyethylene Concentrate Following the general procedure of Example 1, a concentrate of 10% by weight of 2,4,4'-trichloro-2'-hydroxydiphenyl ether (IRGASAN® or IRGAGUARD®, Ciba Specialty Chemicals Corp.) is prepared in low density polyethylene.

Following the general procedure of Example 2, polypropylene homopolymer (100 parts) mixtures without biocide; and with 0.25 and 0.50 parts of the biocide-polyethylene concentrate made above; and with 0.25 and 0.50 parts of the biocide-polyester concentrate made in Example 1. The parts of components are by weight. These mixtures are melt compounded in three passes at 550° F. (288° C.) as seen in Example 2. The extruded pellets are compression molded and the yellowness index (YI) values are determined.

The results are seen in the table below.

| (Biocide % Sample by wt) | Yellowness Index (YI) after multiple pass extrusion at 550° F. (288° C.) | | |
|---|---|---|---|
| | First | Second | Third |
| Control (none) | 8.9 | 8.8 | 12.5 |
| Polyethylene Concentrate (0.25%) | 5.6 | — | 5.0 |
| Polyethylene Concentrate (0.50%) | 9.3 | 11.8 | 10.6 |
| Polyester Concentrate (0.25%) | 0.3 | — | 1.3 |
| Polyester Concentrate (0.50%) | 1.2 | 1.0 | 1.5 |

These results show a far superior performance with regard to color stability of the plaques prepared with the biocide-polyester concentrate as compared to the plaques prepared with the biocide-polyethylene concentrate.

What is claimed is:

1. A biocidaly active polymer composition resistant to discoloration which comprises a melt blend of:
   (I) a polymer substrate, and
   (II) an effective biocidal amount of a biocide-polyester concentrate,
   wherein the polymer substrate is polypropylene or polyethylene;
   which concentrate consists essentially of a biocide (A) and a polyester carrier resin (B),
   wherein the biocide (A) is 10–50% by weight of the concentrate and is selected from the group consisting of:
   (a) 2,4,4'-trichloro-2'-hydroxydiphenyl ether,
   (b) methylene-dithiocyanate, 2-N-octyl-4-isothiazolin-3-one or 3,5-dimethyl-tetrahydro-1,3,5-2H-thiodiazine-2-thione;
   (c) 2-methylithio-4-tert-butylamino-6-cyclopropylamino-s-triazine;
   (d) copper sulfate, copper nitrate or copper-bis(8-hydroxiquilonine);
   (e) tributyltin oxide; and
   (f) silver and zinc compounds or oxy-bis-phenoxyarsine;
   wherein the polyester carrier resin (B) is 90–50% by weight of the concentrate, and
   wherein the biocide (A) is 0.01 to 5% by weight based on the total composition.

2. A composition according to claim 1 wherein the biocide (A) is 2,4,4'-trichloro-2'-hydroxydiphenyl ether.

3. A composition according to claim 1 wherein the polyester carrier resin (B) is a homopolyester or a copolyester prepared from aliphatic, cycloaliphatic or aromatic dicarboxylic acids and diols or hydroxycarboxylic acids.

4. A composition according to claim 3 wherein the polyester (B) has dicarboxylic acid repeating units prepared from dicarboxylic acids selected from the group consisting of terephthalic acidic isophthalic acid, o-phthalic acid, 1,3-, 1,4-, 2,6- and 2,7-naphthalenedicarboxylic acid, 4,4'-biphenyldicarboxylic acid, di(4-carboxyphenyl) sulfone, 4,4'-benzophenonedicarboxylic acid, 1,1,3-trimethyl-5-carboxy-3-(p-carboxyphenyi)indane, di(4-carboxyphenyl) ether, bis(p-carboxy-phenyl)methane and bis(p-carboxyphenyl)ethane.

5. A composition according to claim 4 wherein the dicarboxylic acid is tetphthalic acid, isophthalic acid or 2,6-naphthalenedicarboxylic acid.

6. A composition according to claim 3 wherein the polyester (B) has diol repeating united derived from an aliphatic, cycloaliphatic or aromatic moiety of 2 to 18 carbon atoms.

7. A composition according to claim 6 wherein the diol repeating units are derived from diols selected from the group consisting of ethylene-glycol, diethylene glycol, triethylene glycol, 1,2- and 1,3-propane-diol, 1,2-, 1,3-, 2,3- and 1,4butane diol, pentane-1,5-diol, neopentane glycol, hexane-1,6-diol, dodecane-1,12-diol, 1,4-cyclohexanedimethanol, 3-methylpentane-2,4-diol, 2-methyl-pentanel, 4-diol, 2,2-diethylpropane-1,3-diol, 1,4-di-(hydroxyethoxy)benzene, 2,2-bis(4-hydroxycyclohexyl)-propane, 2,4-dihydroxy-1,1,3,3-tetrarmethylcyclobutane, 2,2-bis-(3-hydroxyethoxyphenyl)-propane, 2,2-bis-(4 hydroxypropoxyphenyl)ethane, 1,4-dihydrdxycyclohexane, p-xylylene glycol, poly(ethylene glycol), poly(propylene glycol), and mixtures thereof.

8. A composition according to claim 7 wherein the diol is 1,4-dihydroxycyclohexane, 1,4-cyclohexanedimethanol, ethylene glycol, 1,4-butanediol, 1,2-propylene-glycol or 1,3trimethylene glycol.

9. A composition according to claim 8 wherein the diol is ethylene glycol.

10. A composition according to claim 3 wherein the polyester (B) is poly(ethylene terephthalate) PET, poly(ethylene 2,6-naphthalene-2,6-dicarboxylate) PEN or poly(ethylene/1,4-cyclo-hexylenedimethylene terephthalate) PETG copolyester.

11. A composition according to claim 10 wherein the polyester (B) is poly(ethylene terephthalate) or poly(ethylene/1,4-cyclohexylenedimethylene terephthalate) copolyester.

12. A composition according to claim 1 wherein the polymer substrate is linear low density polyethylene (LLDPE), low density polyethylene (LDPE) or high density polyethylene (HDPE).

13. A process for preparing a biocidally active polymer composition, which is resistant to discoloration, which comprises
   incorporating an effective biocidal amount of a biocide-polyester concentrate (II) according to claim 1 into a polymer substrate (I) according to claim 1.

* * * * *